United States Patent [19]

Maruyama et al.

[11] Patent Number: 5,498,772
[45] Date of Patent: Mar. 12, 1996

[54] REVERSIBLE HEAT-SENSITIVE RECORDING MATERIAL

[75] Inventors: Jun Maruyama; Kazuyuki Iida; Koichi Torizuka; Shoji Hizatate; Hidekazu Sano; Mitsuhiro Ikeda, all of Tokyo, Japan

[73] Assignee: Mitsubishi Paper Mills Limited, Tokyo, Japan

[21] Appl. No.: 321,523

[22] Filed: Oct. 12, 1994

[30] Foreign Application Priority Data

| Oct. 14, 1993 | [JP] | Japan | 5-256825 |
| Dec. 17, 1993 | [JP] | Japan | 5-317555 |
| Dec. 24, 1993 | [JP] | Japan | 5-328101 |
| Feb. 1, 1994 | [JP] | Japan | 6-010310 |
| Feb. 1, 1994 | [JP] | Japan | 6-010313 |
| Mar. 23, 1994 | [JP] | Japan | 6-051749 |

[51] Int. Cl.$^6$ .................................................. B41M 5/30
[52] U.S. Cl. ........................ 503/216; 503/201; 503/225
[58] Field of Search ............................. 427/150; 503/216, 503/225, 201

[56] References Cited

FOREIGN PATENT DOCUMENTS

| 0248405 | 12/1987 | European Pat. Off. | 503/209 |
| 0373561 | 6/1990 | European Pat. Off. | 503/209 |
| 0492628 | 7/1992 | European Pat. Off. | 503/201 |
| 0524419 | 1/1993 | European Pat. Off. | 503/209 |
| 0574879 | 12/1993 | European Pat. Off. | 503/201 |

*Primary Examiner*—B. Hamilton Hess
*Attorney, Agent, or Firm*—Cushman Darby & Cushman

[57] ABSTRACT

Disclosed is a reversible heat-sensitive recording material comprising a substrate and a recording layer formed thereon, said recording layer comprising a colorless or light-colored, electron-donating dye precursor and a specific electron-accepting compound capable of causing a reversible color tone change of the dye precursor on heating.

7 Claims, No Drawings

REVERSIBLE HEAT-SENSITIVE RECORDING MATERIAL

The present invention relates to a reversible heat-sensitive recording material which permits formation and erasure of an image by heating.

In general, heat-sensitive recording materials are obtained by forming on a substrate a heat-sensitive recording layer composed mainly of a usually colorless or light-colored, electron-donating dye precursor and an electron-accepting developer. On heating with a thermal head, a thermal pen, laser beams or the like, the dye precursor and the developer react with each other in a moment to give a printed image. The heat-sensitive recording materials have been disclosed, for example, in Japanese Patent Laid-Open Nos. 43-4160 and 45-14039.

When an image is once formed in such a heat-sensitive recording material, it is generally impossible to erase the image to restore the heat-sensitive recording material to the former state in which the image has not been formed. Therefore, for recording further infomation, there is no choice but to record the information in a portion of the heat-sensitive recording material where an image has not been formed. Accordingly, when the heat-sensitive recording material is limited in the area of its heat-sensitive recording portion, it has been disadvantageous in that the amount of infomation recorded therein is limited, so that recording of the whole of necessary information is impossible.

In recent years, for coping with such a problem, reversible heat-sensitive recording materials have been devised which permit repeated image formation and image erasion. For example, Japanese Patent Laid-Open Nos. 54-119377, 63-39377 and 63-41186 disclose heat-sensitive recording materials comprising a resin matrix and an organic low-molecular weight compound dispersed therein. But in such a method, the transparency of the heat-sensitive recording materials is reversibly changed by heat energy, so that there is an insufficient contrast between a portion having an image formed therein and a portion having no image formed therein.

In the methods disclosed in Japanese Patent Laid-Open Nos. 50-81157 and 50-105555, an image formed changes with the ambient temperature, so that there is a different between temperatures at which an image-forming state and an image-erasing state, respectively, are maintained. The two states cannot be maintained at ordinary temperature for an optional period of time.

In addition, Japanese Patent Laid-Open No. 59-120492 discloses a method in which an image-forming stateand an image-erasing state are maintained by maintaining a recording material at a temperature in the hysteresis temperature range by utilizing the hysteresis characteristics of a color-developing component. This method is disadvantageous in that a heating sorce and a cooling sorce are necessary for image formation and image erasion, respectively, and that a temperature range in which the image-forming stage and the image-erasing state can be maintained is only in the hysteresis temperature range. Therefore, the method is not suitable for use in a circumstance of daily life temperature.

On the other hand, Japanese Patent Laid-Open Nos. 2-188293 and 2-188294 and International Publication Number WO 90/11898 disclose reversible heat-sensitive recording media comprising a leuco dye and an agent used both as developer and tone reducer which causes color development or achromatization of the leuco dye on heating. The agent used both as developer and tone reducer is an amphoteric compound having an acidic group capable of allowing the leuco dye to develop a color and a basic group capable of achromatizing the leuco dye thus colored. The color development or the achromatization is carried out by causing the color-developing action of the acidic group or the achromatizing action of the basic group, respectively, preferentially by heat energy control. This method, however, does not permit complete switching of the color development reaction and the achromatization reaction over to each other by heat energy control alone. Since the two reactions occur in a certain ratio at the same time, no sufficient coloring density can be attained and no complete achromatization can be carried out. Therefore, no sufficient image contrast can be attained. Moreover, the basic group has achromatizing action also on a colored portion at ordinary temperature, so that the color density of the colored portion is unavoidably decreased with the lapse of time. European Patent Laid-Open No. 492,628 discloses a reversible heat-sensitive recording medium in which a leuco dye is subjected to color development or achromatization by heating. In this reference, as an electron-accepting compound, there are exemplified organophosphate compounds, α-hydroxy aliphatic carboxylic acids, aliphatic dicarboxylic acids, and specific phenol compounds such as alkylthiophenols, alkyloxyphenols, alkylcarbamoylphenols and gallic acid alkyl esters, which have an aliphatic group having 12 or more carbon atoms. This recording medium, however, also cannot solve the two problems, i.e., the low coloring density and the incomplete achromatization at the same time, and is not satisfactory in image stability over a long period of time in practice.

Thus, in prior art, there has not been known a practical reversible heat-sensitive recording material which has a satisfactory image contrast, permits image formation and image erasion, is stable in daily life circumstances over a long period of time, and can maintain a stable image even under conditions severer than the daily life circumstances.

The present invention is intended to provide a reversible heat-sensitive recording material which is satisfactory in practice because it has a marked image contrast, permits image formation and image erasion, is stable in daily life circumstances over a long period of time, can maintain a stable image even under conditions severer than the daily life circumstances, and permits image erasion in a wide temperature range.

The present inventors investigated in order to achieve the above intension, and consequently found the existence of an electron-accepting compound represented by the general formula I, II or III described below which causes a reversible color tone change (i.e. color development and achromatization) of a usually colorless or light-colored, electron-donating dye precursor on heating, whereby the present invention has been accomplished.

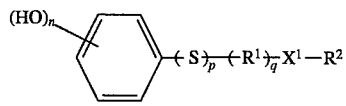

wherein n is an integer of 1 to 3, each of p and q is zero or 1, $R^1$ is a divalent hydrocarbon group having 1 to 18 carbon atoms, R2 is a hydrocarbon group having 1 to 24 carbon atoms, and $X^1$ is a divalent group having at least one —CONE—bond, X1 not including a mere amide and a urea bond in the case of p being zero, and q being 1 in the case of p being 1.

In the compound of the formula I, $R^1$ is a divalent hydrocarbon group having 1 to 18 carbon atoms, preferably a divalent hydrocarbon group having 1 to 12 carbon atoms.

$R^2$ is a hydrocarbon group having 1 to 24 carbon atoms, preferably a hydrocarbon group having 6 to 22 carbon atoms. In addition, the total number of the carbon atoms of $R^1$ and $R^2$ is particularly preferably not more than 35 and not less than 11. Specifically, each of $R^1$ and $R^2$ is chiefly an alkylene or alkyl group which may contain an aromatic ring. In particular, $R^1$ may be an aromatic ring itself. On the other hand, $X^1$ in the formula I is a divalent group having at least one —CONH— bond. Specific examples of $X^1$ are urethane (—NHCOO—, —OCONH—), diacylamine (—CONHCO—), diacylhydrazine (—CONHNHCO—), oxalic diamide (—NHCOCONH—), acylurea (—CONHCONH—, —NHCONHCO—), semicarbazide (—NHCONHNH—, —NHNHCONH—), acylsemicarbazide (—CONHNHCONH—, —NHCONHNHCO—), diacylaminomethane (—CONHCH$_2$NHCO—), 1-acylamino-1-ureidomethane (—CONHCH$_2$NHCONH—, —NHCONHCH$_2$NHCO—), malonamide (—NHCOCH$_2$CONH—), amide (—CONH—, —NHCO—), urea (—NHCONH—), and groups represented by the general formula IV:

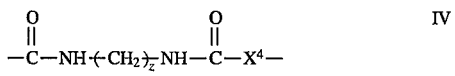

wherein z is zero or 1, and X4 is an oxygen atom or a —NHNH— group.

In the above general formula I, in the case of p being zero, $X^1$ does not include a mere amide (—CONH—, —NHCO—) and a urea bond (—NHCONH—).

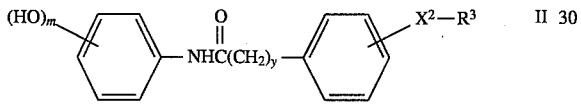

wherein m is 1 or 2, y is an integer of 0 to 2, $X^2$ is a —NHCO— group, —CONH— group, —NHCONH— group, —NHCOCONH— group, —CONHNHCO— group, —CONHNHCONH— group, —CONHNHCOO— group, —OCONH— group, or —NHCOO— group, and $R^3$ is an aliphatic hydrocarbon group.

In the compound of the general formula II, the number of carbon atoms of $R^3$ is preferably large. When the number of carbon atoms of $R^3$ is 5 or less, the compound does not have a sufficient erasing effect. When the number of carbon atoms of $R^3$ is 23 or more, the compound entails great production cost. Therefore, $R^3$ is particularly preferably an aliphatic hydrocarbon group having not more than 22 and not less than 6 carbon atoms.

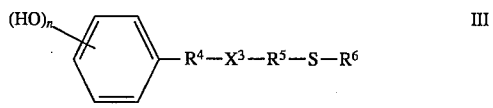

wherein n is an integer of 1 to 3, $R^4$ is a single bond or a divalent hydrocarbon group having 1 to 12 carbon atoms, $R^5$ is a divalent hydrocarbon group having 1 to 12 carbon atoms, $R^6$ is a hydrocarbon group having 1 to 24 carbon atoms, and $X^3$ is a divalent group having at least one —CONH— bond.

In the compound of the formula III, n is an integer of 1 to 3. $R^4$ is a single bond or a divalent hydrocarbon group having 1 to 12 carbon atoms; preferably a single bond or a divalent hydrocarbon group having 1 to 12 carbon atoms which may contain a hetero atom; more preferably a single bond, an alkylene group having 1 to 4 carbon atoms, or an alkylene group having 1 to 10 carbon atoms which contains one or more sulfur atoms or oxygen atoms. $R^5$ is a divalent hydrocarbon group having 1 to 12 carbon atoms, preferably an alkylene group having 2 to 12 carbon atoms. $R^6$ is a hydrocarbon group having 1 to 24 carbon atoms, preferably an alkylene group having 2 to 22 carbon atoms. On the other hand, $X^3$ in the formula III is a divalent group having at least one —CONH— bond. Specific examples of $X^3$ are groups such as amide (—CONH—, —NHCO—), urea (—NHCONH—), diacylamine (—CONHCO—), diacylhydrazine (—CONHNHCO—), oxalic diamide (—NHCOCONH—), acylurea (—CONHCONH—, —NHCONHCO—), semicarbazide (—NHCONHNH—, —NHNHCONH—), acylsemicarbazide (—CONHNHCONH—, —NHCONHNHCO—), diacylaminomethane (—CONHCH$_2$NHCO—), 1-acylamino-1-ureidomethane (—CONHCH$_2$NHCONH—, —NHCONHCH$_2$NHCO—), and malonamide (—NHCOCH$_2$CONH—).

Of the compounds of the general formula I in the present invention, compounds represented by the following general formulas I-1 to I-4 are preferably used.

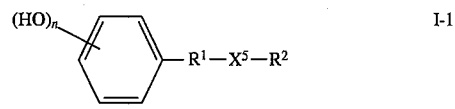

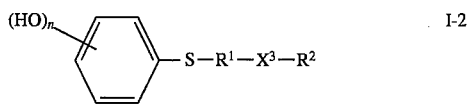

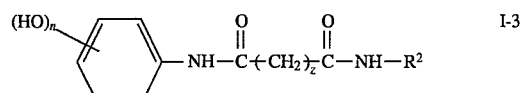

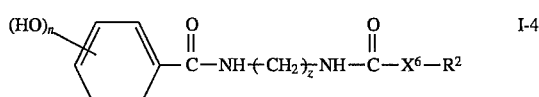

In the above general formulas I-1 to I-4, n, $R^1$ and $R^2$ are as defined in the above general formula I, $X^3$ is as defined in the above general formula III, $X^5$ has the same meaning as that given to $X^1$ in the general formula I in the case of p being zero, z is as defined in the above general formula IV, and $X^6$ is a methylene group, an oxygen atom, a —NH— group or a —NHNH— group.

Specific examples of the electron-accepting compound used in the present invention, i.e., the electron-accepting compound capable of causing a reversible color tone change of a usually colorless or light-colored, electron-donating dye precursor are compounds described below, but these compounds are not intended in any way to limit the scope of the present invention.

The compounds of the general formula I (the general formula I-1) include the following compounds: n-octadecyl N-[2-(p-hydroxyphenyl)ethyl]carbamate, n-tetradecyl N-[6-(p-hydroxyphenyl)hexyl]carbamate, n-dodecyl N-[p-(p-hydroxyphenyl)phenyl]carbamate, [2-(p-hydroxyphenyl)ethyl] N-n-octadecylcarbamate, [11-(p-hydroxyphenyl)undecanyl] N-n-decylcarbamate, [p-(p-hydroxylphenyl)phenyl] N-n-tetradecylcarbamate, N-[3-(p-hydroxyphenyl)propionyl]-N-n-octadecanoylamine, N-[6-(p-hydroxyphenyl)hexanoyl]-N-n-octadecanoylamine, N-[3-(p-hydroxyphenyl)propionyl]-N-(p-n-octylbenzoyl)amine, N-[2-(p-hydroxyphenyl)aceto]-N'-n-dodecanohydrazide, N-[2- (p-hydroxyphenyl)aceto]-N'-n-octadecanohydrazide, N-[3-(p-hydroxyphenyl)propiono]-N'-n-octadecanohydrazide, N-[ 3-(3,4-dihydroxyphenyl)propiono]-N'-n-octadecanohydrazide, N-[2-(p-hydroxyphenyl)aceto]-N'-n-docosanohydrazide, N-[3-(p-hydroxyphenyl)propiono]-N'-n-docosanohydrazide, N-[3-(3,4-dihydroxyphenyl)propiono]-N'-n-docosanohydrazide, N-[6-(p-hydroxyphenyl)hexano]-N'-n-tetradecanohydrazide, N-[6-(p-hydroxyphenyl)hexano]-N'-n-octadecanohydrazide, N-[6-(p-hydroxyphenyl)hexano]-N'-(p-n-octylbenzo)hydrazide, N-[11-(p-hydroxyphenyl)undecano]-N'-n-decanohydrazide, N-[11-(p-hydroxyphenyl)undecano]-N'-n-tetradecanohydrazide, N-[11-(p-hydroxyphenyl)undecano]-N,-n-octadecanohydrazide, N-[11-(p-hydroxyphenyl)undecano]-N'-(6-phenyl)hexanohydrazide, N-[11-(3,4,5-trihydroxyphenyl)undecano]-N'-n-octadecanohydrazide, N-[p-(p-hydroxyphenyl)benzo]-N'-n-octadecanohydrazide, N-[p-(p-hydroxyphenylmethyl)benzo]-N'-n-octadecanohydrazide, N-[2-(p-hydroxyphenyl)ethyl]-N'-n-tetradecyloxamide, N-[3-(p-hydroxyphenyl)propyl]-N'-n-octadecyloxamide, N-[3-( 3,4-dihydroxyphenyl)-propyl]-N'-n-octadecyloxamide, N-[11-(p-hydroxyphenyl)-undecanyl]-N'-n-decyloxamide, N-[p-(p-hydroxyphenyl)-phenyl]-N'-n-octadecyloxamide, N-[2-(p-hydroxyphenyl)-acetyl]-N'-n-dodecylurea, N-[2-(p-hydroxyphenyl)acetyl]-N'-n-octadecylurea, N-[3-(p-hydroxyphenyl)propionyl]-N'-n-octadecylurea, N-[p-(p-hydroxyphenyl)benzoyl]-N'-n-octadecylurea, N-[2-(p-hydroxyphenyl)ethyl]-N'-n-dodecanoylurea, N-[2-(p-hydroxyphenyl)ethyl]-N'-n-octadecanoylurea, N-[p-(p-hydroxyphenyl)phenyl]-N'-n-octadecanoylurea, 4-[2-(p-hydroxyphenyl)ethyl]-1-n-tetradecylsemicarbazide, 4-[2-(p-hydroxyphenyl)ethyl]-1-n-octadecylsemicarbazide, 4-[p-(p-hydroxyphenyl)phenyl]- 1-n-tetradecylsemicarbazide, 1-[2-(p-hydroxyphenyl)-ethyl]- 4-n-tetradecylsemicarbazide, 1-[2-(p-hydroxyphenyl)ethyl]- 4-n-octadecylsemicarbazide, 1-[p-(p-hydroxyphenyl)phenyl]- 4-n-tetradecylsemicarbazide, 1-[2-(p-hydroxyphenyl)acetyl]- 4-n-tetradecylsemicarbazide, 1-[3-(p-hydroxyphenyl)propionyl]-4-n-octadecyl semicarbazide, 1-[11-(p-hydroxyphenyl)undecanoyl]-4-n-decylsemicarbazide, 1-[p-(p-hydroxyphenyl)benzoyl]-4-n-octadecylsemicarbazide, 4-[2-(p-hydroxyphenyl)ethyl]-1-n-tetradecanoylsemicarbazide, 4-[2-(p-hydroxyphenyl)-ethyl]- 1-n-octadecanoylsemicarbazide, 4-[p-(p-hydroxyphenyl)phenyl]- 1-n-octadecanoylsemicarbazide, 1-[2-(p-hydroxyphenyl)acetamido]- 1-n-dodecanoylaminomethane, 1-2-(p-hydroxyphenyl)acetamido]-1-n-octadecanoylaminomethane, 1-[3-(p-hydroxyphenyl)propanamido]-1-n-octadecanoylaminomethane, 1-[11-(p-hydroxyphenyl)-undecanamido]- 1-n-decanoylaminomethane, 1-[p-(p-hydroxyphenyl)benzamido]-1-n-octadecanoylaminomethane, 1-[2-(p-hydroxyphenyl)acetamido]- 1-(3-n-dodecylureido)methane, 1-[2-(p-hydroxyphenyl)acetamido]-1-(3-n-octadecylureido)methane, 1-[3-(p-hydroxyphenyl)propanamido]-1-(3-n-octadecylureido)methane, 1-[11-(p-hydroxyphenyl)-undecanamido]- 1-(3-n-decylureido)methane, 1-[p-(p-hydroxyphenyl)benzamido]- 1-(3-n-octadecylureido)methane, 1-{3-[2-(p-hydroxyphenyl)ethyl]ureido}-1-n-octadecanoylaminomethane, 1-{3-[p-(p-hydroxyphenyl)phenyl]ureido}-1-n-octadecanoylaminomethane, N-[2-(p-hydroxyphenyl)-ethyl]-N'-n-octadecylmalonamide, N-[p-(p-hydroxyphenyl)-phenyl]-N'-n-octadecylmalonamide, etc.

The compounds of the general formula I (the general formula I-2) include the following compounds: N-n-dodecyl- 2-(p-hydroxyphenylthio)acetamide, N-n-octadecyl-2-(p-hydroxyphenylthio)acetamide, N-n-decyl-3-(p-hydroxyphenylthio)propanamide, N-n-octadecyl-3-(p-hydroxyphenylthio)propanamide, N-n-octadecyl-6-(p-hydroxyphenylthio)hexanamide, N-n-decyl-11-(p-hydroxyphenylthio)undecanamide, N-(p-n-octylphenyl)-6-(p-hydroxyphenylthio)hexanamide, N-n-octadecyl-p-(p-hydroxyphenylthio)benzamide, N-(p-hydroxyphenylthio)-methyl-n-dodecanamide, N-(p-hydroxyphenylthio)methyl-n-octadecanamide, N-[2-(p-hydroxyphenylthio)ethyl]-n-octadecanamide, N-[6-(p-hydroxyphenylthio)hexyl]-n-decanamide, N-[p-(p-hydroxyphenylthio)phenyl]-n-octadecanamide, N-(p-hydroxyphenylthio)methyl-N'-n-dodecylurea, N-(p-hydroxyphenylthio)methyl-N'-n-octadecylurea, N-[2-(p-hydroxyphenylthio)ethyl]-N'-n-tetradecylurea, N-[2-(p-hydroxyphenylthio)ethyl]-N'-n-octadecylurea, N-[2-(3,4-dihydroxyphenylthio)ethyl]-N'-n-octadecylurea, N-[6-(p-hydroxyphenylthio)hexyl]-N'-n-decylurea, N-[p-(p-hydroxyphenylthio)phenyl]-N'-n-octadecylurea, N-[10-(p-hydroxyphenylthio)decyl]-N'-n-decylurea, n-octadecyl N-[2-(p-hydroxyphenylthio)ethyl]-carbamate, n-tetradecyl N-[6-(p-hydroxyphenylthio)-hexyl] carbamate, n-dodecyl N-[p-(p-hydroxyphenylthio)-phenyl] carbamate, [2-(p-hydroxyphenylthio)ethyl]N-n-octadecylcarbamate, [11-(p-hydroxyphenylthio)undecyl]N-n-decylcarbamate, [p-(p-hydroxyphenylthio)phenyl]N-n-tetradecylcarbamate, N-[3-(p-hydroxyphenylthio)-propionyl]-N-n-octadecanoylamine, N-[6-(p-hydroxyphenylthio)hexanoyl]-N-n-octadecanoylamine, N-[3-(p-hydroxy phenylthio)propionyl]-N-(p-n-octylbenzoyl)amine, N-[2-(p-hydroxyphenylthio)aceto]-N'-n-dodecanohydrazide, N-[2-(p-hydroxyphenylthio)aceto]-N'-n-octadecanohydrazide, N-[3-(p-hydroxyphenylthio)propiono]-N'-n-octadecano hydrazide, N-[3-(3,4-dihydroxyphenylthio)propiono]-N'-n-octadecanohydrazide, N-[6-(p-hydroxyphenylthio)hexano]-N'-n-tetradecanohydrazide, N-[6-(p-hydroxyphenylthio)hexano]-N'-n-octadecanohydrazide, N-[6-(p-hydroxyphenylthio)hexano]-N'-(p-n-octylbenzo)hydrazide, N-[11-(p-hydroxyphenylthio)undecano]-N'-n-decanohydrazide, N-[11-(p-hydroxyphenylthio)undecano]-N'-n-tetradecanohydrazide, N-[11-(p-hydroxyphenylthio)undecano]-N'-n-octadecanohydrazide, N-[11-(p-hydroxyphenylthio)-undecano]-N'-(6-phenyl)hexanohydrazide, N-[11-(3,4,5-trihydroxyphenylthio)undecano]-N'-n-octadecanohydrazide, N-[p-(p-hydroxyphenylthio)benzo]-N'-n-octadecanohydrazide, N-[p-(p-hydroxyphenylthiomethyl)benzo]-N'-n-octadecanohydrazide, N-[2-(p-hydroxyphenylthio)ethyl]-N'-n-tetradecyloxamide, N-[3-(p-hydroxyphenylthio)-propyl]-N'-n-octadecyloxamide, N-[3-(3,4-dihydroxyphenylthio)propyl]-N'-n-octadecyloxamide, N-[11-(p-hydroxyphenylthio)undecyl]-N'-n-decyloxamide, N-[p-(p-hydroxyphenylthio)phenyl]-N'-n-octadecyloxamide, N-[2-(p-hydroxyphenylthio)acetyl]-N'-n-dodecylurea, N-[2-(p-hydroxyphenylthio)acetyl]-N'-n-octadecylurea, N-[3-(p-hydroxyphenylthio)propionyl]-N'-n-octadecylurea, N-[p-(p-hydroxyphenylthio)benzoyl]-N'-n-octadecylurea, N-[2-(p-hydroxyphenylthio)ethyl]-N'-n-dodecanoylurea, N-[2-(p-hydroxyphenylthio)ethyl]-N'-n-octadecanoylurea, N-[p-(p-hydroxyphenylthio)phenyl]-N'-n-octadecanoylurea, n-octadecyl 3-[3-(p-hydroxyphenylthio)propionyl]-carbazinate, n-decyl 3-[11-(p-hydroxyphenylthio)-undecanoyl]carbazinate, 4-[2-(p-hydroxyphenylthio)-ethyl]- 1-n-tetradecylsemicarbazide, 4-[2-(p-hydroxyphenylthio)ethyl]- 1-n-octadecylsemicarbazide, 4-[p-(p-hydroxyphenylthio)phenyl]- 1-n-tetradecylsemicarbazide, 1-[2-(p-hydroxyphenylthio)ethyl]-4-n-tetradecylsemicarbazide, 1-[2-(p-hydroxyphenylthio)ethyl]-4-n-octadecylsemicarbazide, 1-[p-(p-hydroxyphenylthio)-phenyl]-4-n-tetradecylsemicarbazide, 1-[2-(p-hydroxyphenylthio)acetyl]-4-n-tetradecylsemicarbazide, 1-[3-(p-hydroxyphenylthio)propionyl]-4-n-octadecylsemicarbazide, 1-[11-(p-hydroxyphenylthio- )undecanoyl]-N'-n-decylsemicarbazide, 1-[p-(p-hydroxyphenylthio)benzoyl]-4-n-octadecylsemicarbazide, 4-[2-(p-hydroxyphenylthio)-ethyl]-1-n-tetradecanoylsemicarbazide, 4-[2-(p-hydroxyphenylthio)ethyl]- 1-n-octadecanoylsemicarbazide, 4-[p-(p-hydroxyphenylthio)phenyl]-1-n-octadecanoylsemicarbazide, 1-[2-(p-hydroxyphenylthio)acetamido]-1-n-dodecanoylaminomethane, 1-[2-(p-hydroxyphenylthio)-acetamido]- 1-n-octadecanoylaminomethane, 1-[3-(p-hydroxyphenylthio)propanamido]- 1-n-octadecanoylaminomethane, 1-[11-(p-hydroxyphenylthio)undecanamido]-N'-n-decanoylaminomethane, 1-[p-(p-hydroxyphenylthio)benzamido]- 1-n-octadecanoylaminomethane, 1-[2-(p-hydroxyphenylthio)acetamido]- 1-(N'-n-dodecylureido)methane, 1-[2-(p-hydroxyphenylthio)acetamido]-1-(N'-n-octadecylureido)methane, 1-[3-(p-hydroxyphenylthio)propanamido]- 1-(N'-n-octadecylureido)methane, 1-[11-(p-hydroxyphenylthio)undecanamido]-N'-(N,-decylureido)-methane, 1-[p-(p-hydroxyphenylthio)benzamido]-1-(N,-n-octadecylureido)methane, 1-{N,-[2-(p-hydroxyphenylthio)-ethyl]ureido}- 1-n-octadecanoylaminomethane, 1-{N'-[p-(p- hydroxyphenylthio)phenyl]ureido}- 1-n-octadecanoylamino-methane, N-[2-(p-hydroxyphenylthio)ethyl]-N'-n' octadecylureido)methane, octadecylmalonamide, N-[p-(p-hydroxyphenylthio)phenyl]-N'-n-octadecylmalonamide, etc.

The compounds of the general formula I (the general formula I-3) include the following compounds: N-(p-hydroxyphenyl)-N'-n-hexylmalonamide, N-(p-hydroxyphenyl)-N'-n-decylmalonamide, N-(p-hydroxyphenyl)-N'-n-octadecylmalonamide, N-(p-hydroxyphenyl)-N'-n-oleylmalonamide, N-(p-hydroxyphenyl)-N'-(p-n-heptylphenyl)malonamide, N-(p-hydroxyphenyl)-N'-(p-n-octadecyloxyphenyl)malonamide, N-(3,4-dihydroxyphenyl)-N'-n-hexylmalonamide, N-(3,4-dihydroxyphenyl)-N'-n-decylmalonamide, N-(3,4-dihydroxyphenyl)-N'-n-octadecylmalonamide, N-(3,4-dihydroxyphenyl)-N'-n-oleylmalonamide, N-(3,4-dihydroxyphenyl)-N'-(p-n-heptylphenyl)malonamide, N-(3, 4-dihydroxyphenyl)-N'-(p-n-octadecyloxyphenyl)malonamide, N-(3,4,5-trihydroxyphenyl)-N'-n-hexylmalonamide, N-(3,4,5-trihydroxyphenyl)-N'-n-decylmalonamide, N-(3,4,5-trihydroxyphenyl)-N'-n-octadecylmalonamide, N-(3,4,5-trihydroxyphenyl)-N'-n-oleylmalonamide, N-(3,4,5-trihydroxyphenyl)-N'-(p-n-heptylphenyl)malonamide, N-(3, 4,5-trihydroxyphenyl)-N'-(p-n-octadecyloxyphenyl)-malonamide, N-(p-hydroxyphenyl)-N'-n-hexyloxamide, N-(p-hydroxyphenyl)-N'-n-decyloxamide, N-(p-hydroxyphenyl)-N'-n-octadecyloxamide, N-(p-hydroxyphenyl)-N'-n-oleyloxamide, N-(p-hydroxyphenyl)-N'-(p-n-heptylphenyl)-oxamide, N-(p-hydroxyphenyl)-N'-(p-n-octadecyloxyphenyl)oxamide, N-(3,4-dihydroxyphenyl)-N'-n-hexyloxamide, N-(3,4-dihydroxyphenyl)-N'-n-decyloxamide, N-(3,4-dihydroxyphenyl)-N'-n-octadecyloxamide, N-(3,4-dihydroxyphenyl)-N'-n-oleyloxamide, N-(3,4-dihydroxyphenyl)-N'-(p-n-heptylphenyl)oxamide, N-(3,4-dihydroxyphenyl)-N'-(p-n-octadecyloxyphenyl)oxamide, N-(3,4,5-trihydroxyphenyl)-N'-n-hexyloxamide, N-(3,4,5-trihydroxyphenyl)-N'-n-decyloxamide, N-(3,4,5-trihydroxyphenyl)-N'-n-octadecyloxamide, N-(3,4,5-trihydroxyphenyl)-N'-n-oleyloxamide, N-(3,4,5-trihydroxyphenyl)-N'-(p-n-heptylphenyl)oxamide, N-(3,4,5-trihydroxyphenyl)-N'-(p-n-octadecyloxyphenyl)oxamide, etc.

The compounds of the general formula I (the general formula I-4) include the following compounds: N-(4-hydroxybenzoyl)-N'-n-octanoylhydrazine, N-(4-hydroxybenzoyl)-N'-n-dodecanoylhydrazine, N-(4-hydroxybenzoyl)-N'-n-tetradecanoylhydrazine, N-(4-hydroxybenzoyl)-N'-n-octadecanoylhydrazine, N-(2,4-dihydroxybenzoyl)-N'-n-octanoylhydrazine, N-(2,4-dihydroxybenzoyl)-N'-n-dodecanoylhydrazine, N-(2,4-dihydroxybenzoyl)-N'-n-tetradecanoylhydrazine, N-(2,4-dihydroxybenzoyl)-N'-n-octadecanoylhydrazine, N-(4-hydroxybenzoyl)-N'-n-octylaminocarbonylhydrazine, N-(4-hydroxybenzoyl)-N'-n-dodecylaminocarbonylhydrazine, N-(4-hydroxybenzoyl)-N'-n-tetradecylaminocarbonylhydrazine, N-(4-hydroxybenzoyl)-N'-n-octadecylaminocarbonylhydrazine, N-(2,4-dihydroxybenzoyl)-N'-n-octylaminocarbonylhydrazine, N-(2,4-dihydroxybenzoyl)-N'-n-dodecylaminocarbonylhydrazine, N-(2,4-dihydroxybenzoyl)-N'-n-tetradecylaminocarbonylhydrazine, N-(2,4-dihydroxybenzoyl)-N'-n-octadecylaminocarbonylhydrazine, N-(4-hydroxybenzoyl)-N'-n-octyloxycarbonylhydrazine, N-(4-hydroxybenzoyl)-N'-n-dodecyloxycarbonylhydrazine, N-(4-hydroxybenzoyl)-N'-n-tetradecyloxycarbonylhydrazine, N-(4-hydroxybenzoyl)-N-n-octadecyloxycarbonylhydrazine, N-(2,4-dihydroxybenzoyl)-N'-n-octyloxycarbonylhydrazine, N-(2,4-dihydroxybenzoyl)-N'-n-dodecyloxycarbonylhydrazine, N-(2,4-dihydroxybenzoyl)-N'-n-tetradecyloxycarbonylhydrazine, N-(2,4-dihydroxybenzoyl)-N'-n-octadecyloxycarbonylhydrazine, N-(4-hydroxybenzoyl)-N'-n-octylhydrazinocarbonylhydrazine, N-(4-hydroxybenzoyl)-N'-n-dodecylhydrazinocarbonylhydrazine, N-(4-hydroxybenzoyl)-N'-n-tetradecylhydrazinocarbonylhydrazine, N-(4-hydroxybenzoyl)-N'-n-octadecylhydrazinocarbonylhydrazine, N-(2,4-dihydroxybenzoyl)-N'-n-octylhydrazinocarbonylhydrazine, N-(2,4-dihydroxybenzoyl)-N'-n-dodecylhydrazinocarbonylhydrazine, N-(2,4-dihydroxybenzoyl)-N'-n-tetradecylhydrazinocarbonylhydrazine, N-(2,4-dihydroxybenzoyl)-N'-n-octadecylhydrazinocarbonylhydrazine, N-(4-hydroxybenzoyl)-N'-n-octanoylmethylenediamine, N-(4-hydroxybenzoyl)-N'-n-dodecanoylmethylenediamine, N-(4-hydroxybenzoyl)-N'-n-tetradecanoylmethylenediamine, N-(4-hydroxybenzoyl)-N'-n-octadecanoylmethylenediamine, N-(2,4-dihydroxybenzoyl)-N'-n-octanoylmethylenediamine, N-(2,4-dihydroxybenzoyl)-N'-n-dodecanoylmethylenediamine, N-(2,4-dihydroxybenzoyl)-N'-n-tetradecanoylmethylenediamine, N-(2,4-dihydroxybenzoyl)-N'-n-octadecanoylmethylenediamine, N-(4-hydroxybenzoyl)-N'-n-octylaminocarbonylmethylenediamine, N-(4-hydroxybenzoyl)-N'-n-dodecylaminocarbonylmethylenediamine, N-(4-hydroxybenzoyl)-N'-n-tetradecylaminocarbonylmethylenediamine, N-(4-hydroxybenzoyl)-N'-n-octadecylaminocarbonylmethylenediamine, N-(2,4-dihydroxybenzoyl)-N'-n-octylaminocarbonylmethylenediamine, N-(2,4-dihydroxybenzoyl)-N'-n-dodecylaminocarbonylmethylenediamine, N-(2,4-dihydroxybenzoyl)-N'-n-tetradecylaminocarbonylmethylenediamine, N-(2,4-dihydroxybenzoyl)-N'-n-octadecylaminocarbonylmethylenediamine, N-(4-hydroxybenzoyl)-N'-n-octyloxycarbonylmethylenediamine, N-(4-hydroxybenzoyl)-N'-n-dodecyloxycarbonylmethylenediamine, N-(4-hydroxybenzoyl)-N'-n-tetradecyloxycarbonylmethylenediamine, N-(4-hydroxybenzoyl)-N'-n-octadecyloxycarbonylmethylenediamine, N-(2,4-dihydroxybenzoyl)-N'-n-octyloxycarbonylmethylenediamine, N-(2,4-dihydroxybenzoyl)-N'-n- dodecyloxycarbonylmethylenediamine, N-(2,4-dihydroxybenzoyl)-N'-n-tetradecyloxycarbonylmethylenediamine, N-(2,4-dihydroxybenzoyl)-N'-n-octadecyloxycarbonylmethylenediamine, N-(4-hydroxybenzoyl)-N'-n-octylhydrazinocarbonylmethylenediamine, N-(4-hydroxybenzoyl)-N'-n-dodecylhydrazinocarbonylmethylenediamine, N-(4-hydroxybenzoyl)-N'-n-tetradecylhydrazinocarbonylmethylenediamine, N-(4-hydroxybenzoyl)-N'-n-octadecylhydrazinocarbonylmethylenediamine, N-(2,4-dihydroxybenzoyl)-N'-n-octylhydrazinocarbonylmethylenediamine, N-(2,4-dihydroxybenzoyl)-N'-n-dodecylhydrazinocarbonylmethylenediamine, N-(2,4-dihydroxybenzoyl)-N'-n-tetradecylhydrazinocarbonylmethylenediamine, N-(2,4-dihydroxybenzoyl)-N'-n-octadecylhydrazinocarbonylmethylenediamine, etc.

As the compound of the general formula II, the following compounds can be exemplified:

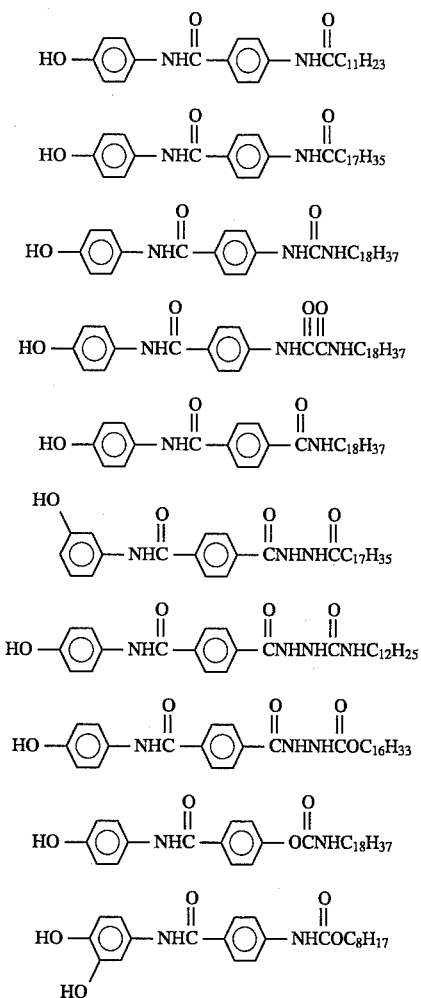

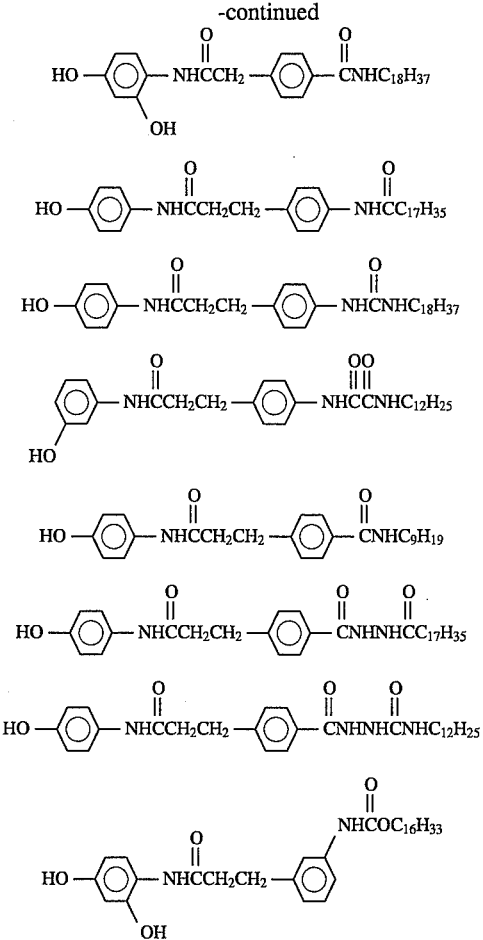

As the compound of the general formula III, the following compounds can be exemplified: N-12-thiadocosyl-4-hydroxybenzamide, N-12-thiadocosyl-3,4,5-trihydroxybenzamide, N-12-thiadocosyl-3-(4-hydroxypheyl)propanoylamide, N-4-hydroxyphenyl-4-thiahexadecanamide, N-4-hydroxyphenyl-12-thiadocosanamide, N-4-hydroxyphenyl-N'-12-thiadocosylurea, N-4-thiahexadecanoyl-4-hydroxybenzamide, N-12-thiadocosanoyl-4-hydroxybenzamide, N-4-thiahexadecanoyl-3,4,5-trihydroxybenzamide, N-12-thiadocosanoyl-3,4,5-trihydroxybenzamide, N-4-thiahexadecanoyl-3-(4-hydroxyphenyl)-propanoylamide, N-12-thiadocosanoyl-3-(4-hydroxyphenyl)-propanoylamide, N-4-hydroxybenzono-N'-4-thiahexadecanohydrazide, N-4-hydroxybenzono-N'-12-thiadocosanohydrazide, N-3-(4-hydroxyphenyl)propano-N'-4-thiahexadecanohydrazide, N-3-(4-hydroxyphenyl)propano-N'-12-thiadocosanohydrazide, N-11-(4-hydroxyphenylthio)-undecano-N'-4-thiahexadecanohydrazide, N-11-(4-hydroxyphenylthio)undecano-N'-12-thiadocosanohydrazide, N-3,4,5-trihydroxybenzono-N'-4-thiahexadecanohydrazide, N-3,4,5-trihydroxybenzono-N'-12-thiadocosanohydrazide, N-4-hydroxyphenyl-N'-12-thiadocosyloxamide, N-4-hydroxybenzoyl-N'-12-thiadocosylurea, N-4-thiahexadecanoyl-N'-4-hydroxyphenylurea, N-12-thiadocosanoyl-N'-4-hydroxyphenylurea, 1-(4-hydroxyphenyl)-4-(12-thiadocosyl)-semicarbazide, 1-(4-hydroxybenzoyl)-4-(12-thiadocosyl)-semicarbazide, 1-(4-thiahexadecanoyl)-4-(4-hydroxyphenyl)semicarbazide, 1-(12-thiadocosanoyl)-4-(4-hydroxyphenyl)semicarbazide, 1-(4-hydroxybenzamido)-1-(4-thiahexadecanoylamino)methane, and 1-(4-hydroxybenzamido)-1-(12-thiadocosanoylamino)methane.

As the electron-accepting compound according to the present invention, the above-exemplified compounds may be used singly or as a mixture of two or more thereof. The amount of the electron-accepting compound used is 5 to 5,000% by weight, preferably 10 to 3,000% by weight, based on the weight of the usually colorless or light-colored dye precursor.

The usually colorless or light-colored, electron-donating dye precursor is represented by those generally used in pressure-sensitive recording paper, heat-sensitive recording paper, etc. but is not particularly limited. Specific examples of the electron-donating dye precursor are as follows but they are not intended in any way to limit the scope of the present invention:

(1) Triarylmethane type compounds 3,3-bis(p-dimethylaminophenyl)-6-dimethylaminophthalide (Crystal Violet lactone), 3,3-bis(p-dimethylaminophenyl)phthalide, 3-(p-dimethylaminophenyl)- 3-(1,2-dimethylindol-3-yl)phthalide, 3-(p-dimethylaminophenyl)- 3-(2-methylindol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-bis(2-phenylindol-3-yl)-5-dimethylaminophthalide, 3-p-dimethylaminophenyl-3-(1-methylpyrrol-2-yl)-6-dimethylaminophthalide, etc. (2) Diphenylmethane type compounds 4,4'-bis(dimethylaminophenyl)benzhydryl benzyl ether, N-chlorophenylleucoauramine, N-2,4,5-trichlorophenylleucoauramine, etc.

(3) Xanthene type compounds

Rhodamine B anilinolactam, Rhodamine B-p-chloroanilinolactam, 3-diethylamino-7-dibenzylaminofluoran, 3-diethylamino-7-octylaminofluoran, 3-diethylamino-7-phenylfluoran, 3-diethylamino-7-chlorofluoran, 3-diethylamino-6-chloro-7-methylfluoran, 3-diethylamino-7-(3,4-dichloroanilino)fluoran, 3-diethylamino-7-( 2-chloroanilino)fluoran, 3-diethylamino-6-methyl-7-anilinofluoran, 3-(N-ethyl)tolylamino-6-methyl-7-anilinofluoran, 3-piperidino-6-methyl-7-anilinofluoran, 3-(N-ethyl)tolylamino-6-methyl-7-phenethylfluoran, 3-diethylamino-7-(4-nitroanilino)fluoran, 3-dibutylaminomethyl-7-anilinofluoran, 3-(N-methyl)propylamino-6-methyl-7-anilinofluoran, 3-( N-ethyl)isoamylamino-6-methyl-7-anilinofluoran, 3-( N-methyl)cyclohexylamino-6-methyl-7-anilinofluoran, 3-(N-ethyl)tetrahydrofurylamino-6-methyl-7-anilinofluoran, etc.

(4) Thiazine type compounds benzoylleucomethylene blue, p-nitrobenzoylleucomethylene blue, etc.

(5) Spiro-compounds 3-methylspirodinaphthopyran, 3-ethylspirodinaphthopyran, 3,3'-dichlorospirodinaphthopyran, 3-benzylspirodinaphthopyran, 3-methylnaphtho-(3-methoxybenzo)spiropyran, 3-propylspirobenzopyran, etc.

The above-exemplified usually colorless or light-colored dye precursors may be used singly or as a mixture of two or more thereof.

Next, a concrete process for producing the reversible heat-sensitive recording material of the present invention is described below but it is not intended in any way to limit the scope of the present invention.

A specific example of process for producing the reversible heat-sensitive recording material of the present invention is a process in which a usually colorless or light-colored dye precursor and the electron-accepting compound according to the present invention are used as main components and applied or printed on a substrate to form a reversible heat-sensitive recording layer.

As a method for incorporating the usually colorless or light-colored dye precursor and the electron-accepting compound according to the present invention into the reversible heat-sensitive recording layer, there can be exemplified a method of dissolving each of these compounds in a solvent or dispersing each compound in a dispersion medium and mixing the resulting solutions or dispersions, a method of mixing the compounds and dissolving the resulting mixture in a solvent or dissolving the mixture in a dispersion medium, and a method of melting each compound by heating to homogenize the same, cooling the homogenized compounds, and then dissolving them in a solvent or dispersing them in a dispersion medium. But the method for the incorporation is not specified.

A binder may be incorporated into the reversible heat-sensitive recording layer for the purpose of, for example, improving the strength of the reversible heat-sensitive recording layer. Specific examples of the binder are water-soluble macromolecules such as starches, hydroxyethyl cellulose, methyl cellulose, carboxymethyl cellulose, gelatin, casein, poly(vinyl alcohol)s, modified poly(vinyl alcohol)s, sodium poly(acrylate)s, acrylamide-acrylic ester copolymers, acrylamide-acrylic ester-methacrylic ester terpolymers, alkali salts of styrene-maleic anhydride copolymers, alkali salts of ethylene-maleic anhydride copolymers, etc.; and latices of poly(vinyl acetate)s, polyurethanes, poly(acrylic ester)s, styrene-butadiene copolymers, acrylonitrile-butadiene copolymers, methyl acrylate-butadiene copolymers, ethylene-vinyl acetate copolymers, etc. The binder is not limited to them.

A heat-meltable material may be incorporated into the reversible heat-sensitive recording layer as an additive for controlling the color development sensitivity and achromatization temperature of the reversible heat-sensitive recording layer. The heat-meltable material is preferably one which has a melting point of 60°–200° C., more preferably 80°–180° C. Sensitizers used in ordinary heat-sensitive recording paper may be used. There may be incorporated a combination of sensitizers selected from the group consisting of, for example, waxes (e.g. N-hydroxymethylstearamide, stearamide and palmitamide), naphthol derivatives (e.g. 2-benzyloxynaphthalene), biphenyl derivatives (e.g. p-benzylbiphenyl and 4-allyloxybiphenyl), polyether compounds [e.g. 1,2-bis(3-methylphenoxy)ethane, 2,2'-bis(4-methoxyphenoxy)diethyl ether and bis(4-methoxyphenyl) ether], and carbonic or oxalic diester derivatives [e.g. diphenyl carbonate, dibenzyl oxalate and bis(p-methylbenzyl) oxalate].

As a substrate used in the reversible heat-sensitive recording material of the present invention, there may be optionally used, depending on purposes, paper, various nonwoven fabrics, woven fabrics, synthetic resin films, synthetic resin laminated papers, synthetic papers, metal foils, glass, and composite sheets obtained by combining two or more of them. The substrate may be transparent, semitransparent or opaque. The substrate is not limited to the above-exemplified materials.

The reversible heat-sensitive recording material of the present invention may be composed of a reversible heat-sensitive recording layer alone. If necessary, a protective layer may be formed on the reversible heat-sensitive recording layer. An intermediate layer may also be formed between the reversible heat-sensitive recording layer and the substrate. In this case, the protective layer and/or the intermediate layer may be composed of two or more layers. In addition, a material capable of recording information electrically, magnetically or optically may be contained in the reversible heat-sensitive recording layer and/or any of the other layers, and/or on the side of the substrate on which the reversible heat-sensitive recording layer is formed and/or the reverse side. For preventing curling and electrification, a back coating layer may be formed on the side reverse to the side having the reversible heat-sensitive recording layer formed thereon.

The reversible heat-sensitive recording layer can be formed, for example, by a method of mixing dispersions obtained by fine grinding of each color-producing component, applying or printing the resulting mixture on a substrate, and drying the mixture; or a method of mixing solutions obtained by dissolving each color-producing component in a solvent, applying or printing the resulting mixture on a substrate, and drying the mixture. In this case, for example, it is also possible to form a multi-layer structure by incorporating each color-producing component into one layer.

In addition, the reversible heat-sensitive recording layer and/or the protective layer, and/or the intermediate layer may contain, for example, pigments such as diatomaceous earth, talc, kaolin, calcined kaolin, calcium carbonate, magnesium carbonate, titanium oxide, zinc oxide, silicon oxide, aluminum hydroxide, urea-formaldehyde resin, etc.; metal salts of higher fatty acids, such as zinc stearate, calcium stearate, etc.; waxes such as paraffin, oxidized paraffin, polyethylenes, oxidized polyethylene, stearamide, castor wax, etc.; dispersing agents such as sodium dioctylsulfosuccinate, etc.; surfactants; and fluorescent dyes.

The electron-accepting compound according to the present invention has also a achromatizing effect, i.e., a reversing effect specifically in spite of its ability to allow a leuco dye to develop a color. This fact is entirely unexpected. Such a reversing effect is not brought about at all by electron-accepting compounds used in conventional heat-sensitive recording materials, for example, 2,2-bis(4-hydroxyphenyl)propane, bis(4-hydroxyphenyl)sulfone, and benzyl 4-hydroxybenzoate.

Although the principle of the image formation and image erasure in the heat-sensitive recording material of the present invention is unexplained, the following is conjectured. When the usually colorless or light-colored dye precursor is heated together with the electron-accepting compound such as a phenolic compound, it develops a color owing to electron transfer from the dye precursor to the electron-accepting compound. In this case, it can be speculated that molecules of the electron-accepting compound are quite close to molecules of the dye thus colored. When the molecules of the electron-accepting compound are separated from the molecules of the dye colored, the molecules of the dye colored receive electrons to return to the dye precursor state before the color development. It is conjectured that in the present invention, the color development and achromatization are carried out by changing the distance between molecules of the electron-accepting compound and molecules of the dye by heating.

In detail, it is conjectured that since the electron-accepting compound according to the present invention has a large aliphatic chain in the molecule, it has a bad compatibility with molecules of the dye precursor and molecules of the dye which has developed a color, so that the electron-accepting compound and molecules of the dye precursor or the dye colored are hardly soluble in each other in a solid state. In a state in which molecules of the dye precursor and molecules of the electron-accepting compound according to the present invention can move freely, for example, a molten state brought about by heating, molecules of the dye precursor and molecules of the electron-accepting compound according to the present invention are soluble in each other in a certain ratio, so that color development occurs. Therefore, when the colored and molten mixture thus obtained is slowly cooled, the electron-accepting compound according to the present invention and molecules of the dye becomes insoluble in each other with a lowering of the temperature to undergo phase separation, resulting in achromatization. In this case, the electron-accepting compound according to the present invention is rapidly crystallized due to its intermolecular hydrogen bonds because it has in the molecule a connecting group having hydrogen-linking ability such as amide group. On the other hand, when rapidly cooled, the mixture is solidified before phase separation, namely, it is solidified in a colored state. Therefore, the colored state is fixed and hence is stably maintained also after the solidification.

It can be speculated that as described above, the reversible heat-sensitive recording material of the present invention shows color development and achromatization by creating a state in which molecules of the dye and the electron-accepting compound according to the present invention are compatible with each other and a state in which the dye molecules and the compound undergo phase separation. To carry out the color development, heating followed by rapid cooling is sufficient. The color development can be carried out, for example, by heating with a thermal head, laser beams or the like. Slow cooling after the heating causes the achromatization. The achromatization can be carried out by means of, for example, a heating roll, heating stamp, thermal head, high-frequency heater, hot air, electric heater, or radiant heat from a light source such as a halogen lamp.

Typical and specific synthesis examples of the electron-accepting compound used in the present invention are described below.

Synthesis examples of compounds of the general formula I (the general formula I-1)

Synthesis Example 1

Synthesis of N-[2-(p-hydroxyphenyl)aceto]-N'-n-octadecanohydrazide

Into a 100-ml flask equipped with a stirrer were charged 3.3 g of p-hydroxyphenylacetohydrazide, 2.1 g of triethylamine and 30 ml of dimethylacetamide, and heated to effect dissolution. Thereto was added dropwise 5.7 g of octadecanoyl chloride at room temperature, and the resulting mixture was stirred at room temperature for 1 hour. The solid formed by the reaction was dissolved by heating and poured into a mixture of 100 ml of diluted hydrochloric acid and 30 g of ice. The crystals precipitated were collected by filtration and washed with hot benzene and then hot isopropanol to obtain 7.3 g of the desired compound. Melting point: 201° C.

Synthesis Example 2

Synthesis of N-[3-(p-hydroxyphenyl)propiono]-N'-n-octadecanohydrazide

Into a 100-ml flask equipped with a stirrer were charged 3.6 g of p-hydroxyphenylpropionohydrazide, 2.1 g of triethylamine and 30 ml of dimethylacetamide, and heated to effect dissolution. Thereto was added dropwise 5.7 g of octadecanoyl chloride at room temperature, and the resulting mixture was stirred at room temperature for 1 hour. The solid formed by the reaction was once dissolved by heating and poured into a mixture of 100 ml of diluted hydrochloric acid and 30 g of ice. The crystals precipitated were collected by filtration and recrystallized from isopropanol to obtain 7.3 g of the desired compound. Melting point: 171° C.

Synthesis Example 3

Synthesis of N-[5-(p-hydroxyphenyl)valeryl]-N'-n-docosanohydrazide

Into a 100-ml flask equipped with a stirrer were charged 2.1 g of p-hydroxyphenylvalerohydrazide, 1.1 g of triethylamine and 20 ml of dimethylacetamide, and heated to effect dissolution. Thereto was added dropwise acid chloride separately synthesized from 3.4 g of behenic acid and 1.9 g of oxalyl chloride, and the resulting mixture was stirred at room temperature for 1 hour. The solid formed by the reaction was once dissolved by heating and poured into a mixture of 50 ml of diluted hydrochloric acid and 15 g of ice. The crystals precipitated were collected by filtration and recrystallized from isopropanol to obtain 4.4 g of the desired compound. Melting point: 146° C.

Synthesis Example 4

Synthesis of 1-(p-hydroxyphenyl)acetamido-1-n-octadecanoylaminomethane

Into a 200-ml flask equipped with a stirrer and a condenser were charged 13.2 g of p-hydroxyphenylacetamide, 20.0 g of N-hydroxymethyl-n-octadecanamide, 5 drops of concentrated hydrochloric acid and 140 ml of tetrahydrofuran, and stirred with heating at 60° C. for 5 hours. The reaction mixture was cooled to room temperature and then poured into 300 ml of distilled water. The crystals precipitated were collected by filtration and recrystallized from isopropanol to obtain 18.6 g of the desired compound. Melting point: 176° C.

Synthesis Example 5

Synthesis of N-[2-(p-hydroxyphenyl)ethyl]-N'-n-octadecyloxamide

Into a 100-ml flask equipped with a stirrer were charged 5.2 g of tyramine hydrochloride and 40 ml of actonitrile, and 7.6 g of triethylamine was added under ice-cooling. Then, 4.1 g of ethyl chloroglyoxylate was added dropwise over a period of 30 minutes, and the resulting mixture was stirred at the same temperature for 1 hour. The reaction mixture was poured into a mixture of 100 ml of diluted hydrochloric acid and 15 g of ice, followed by two times of extraction with ethyl acetate. The combined organic layer was washed successively with diluted hydrochloric acid, distilled water and a saturated aqueous sodium chloride solution. The washed organic layer was dried over anhydrous magnesium sulfate, and distilled under reduced pressure to remove the solvent. The oil thus obtained was dissolved in 300 ml of ethanol, followed by adding thereto 8.2 g of octadecylamine, and the resulting mixture was heated under reflux for 30 minutes. The reaction mixture was cooled to room temperature, after which the crystals precipitated were collected by filtration to obtain 8.8 g of the desired compound. Melting point: 167° C.

Synthesis examples of compounds of the general formula I (the general formula I-2)

Synthesis Example 6

Synthesis of N-[2-(p-hydroxyphenylthio)ethyl]-N'-n-octadecylurea

Into a 200-ml flask equipped with a stirrer and a condenser were charged 10.0 g of 2-(p-hydroxyphenylthio)ethylamine and 120 ml of methyl ethyl ketone, and stirred with heating at 60° C. in a nitrogen stream. Into the resulting solution was slowly dropped 15.3 g of n-octadecyl isocyanate, upon which white crystals were immediately precipitated. The reaction temperature was raised to 90° C. and stirring was continued with heating for 1 hour. The reaction mixture was cooled to room temperature, after which the crystals precipitated were collected by filtration. Recrystallization from chloroform gave 27.5 g of the desired compound. Melting point: 121° C.

Synthesis Example 7

Synthesis of N-[11-(p-hydroxyphenylthio)undecano]-N'-n-decanohydrazide

Into a 200-ml flask equipped with a stirrer and a condenser were charged 12.0 g of [11-(p-hydroxyphenylthio)undecano]hydrazide, 2.86 g of triethylamine and 140 ml of dimethylacetamide, and stirred under ice-cooling in a nitrogen stream. Into the resulting solution was slowly dropped 6.76 g of n-decanoyl chloride, upon which white crystals were precipitated. After standing at room temperature for 24 hours, the crystals were added to 300 ml of distilled water and the crystals precipitated were collected by filtration. Recrystallization from isopropanol gave 14.4 g of the desired compound. Melting point: 161° C.

Synthesis Example 8

Synthesis of N-[p-(p-hydroxyphenylthiomethyl)benzo]-N'-n-octadecanohydrazide

Into a 200-ml flask equipped with a stirrer and a condenser were charged 4.7 g of p-hydroxythiophenol, 14.0 g of N-(p-chloromethylbenzo)-N'-n-octadecanohydrazide, 2.1 g of potassium hydroxide and 130 ml of methanol, and stirred with heating at 50° C. for 6 hours in a nitrogen stream. The reaction mixture was cooled to room temperature and then poured into 300 ml of distilled water. The white crystals precipitated were collected by filtration and recrystallized from isopropanol to obtain 13.8 g of the desired compound. Melting point: 164° C.

Synthesis Example 9

Synthesis of N-[p-(p-hydroxyphenylthio)phenyl]-N'-octadecyloxamide

Into a 200-ml flask equipped with a stirrer and a condenser were charged 57.1 g of ethyl N-p-(p-hydroxyphenylthio)phenyloxamate, 3.4 g of n-octadecylamine and 120 ml of ethanol, and heated under reflux to precipitate crystals. The reflux was continued for 1 hour, after which the reaction mixture was cooled to room temperature and the cystals were collected by filtration. Recrystallization from isopropanol gave 5.2 g of the desired compound. Melting point: 163° C.

Synthesis Example 10

Synthesis of 1-[3-(p-hydroxyphenylthio)-propanamido]-1-n-octadecanoylaminomethane Into a 200-ml flask equipped with a stirrer and a condenser were charged 8.0 g of 3-(p-hydroxyphenylthio)propanamide, 10.6 g of N-hydroxymethyl-n-octadecanamide, 5 drops of concentrated hydrochloric acid and 120 ml of tetrahydrofuran, and stirred with heating at 60° C. for 5 hours. The reaction mixture was cooled to room temperature and then poured into 300 ml of distilled water. The white crystals precipitated were collected by filtration and recrystallized from isopropanol to obtain 12.0 g of the desired compound. Melting point: 172° C.

Synthesis examples of a compound of the general formula I (the general formula I-3)

Synthesis Example 11

Synthesis of N-(p-hydroxyphenyl)-N'-n-octadecyl-oxamide

Into a 300-ml flask equipped with a stirrer were charged 5.5 g of p-aminophenol, 5.6 g of triethylamine and 150 ml of acetonitrile, and heated to effect dissolution. Thereto was added dropwise 6.8 g of ethyl chloroglyoxylate under ice-cooling, and the resulting mixture was stirred at the same temperature for 1 hour. The reaction mixture was poured into ice-cooled hydrochloric acid and subjected to salting-out, followed by two times of extraction with ethyl acetate. The combined organic layer was washed successively with diluted hydrochloric acid, distilled water and a saturated aqueous sodium chloride solution. The washed organic layer was dried over anhydrous magnesium sulfate, and distilled under reduced pressure to remove the ethyl acetate. To the residue were added 200 ml of ethanol and 9.4 g of stearylamine, and the resulting mixture was heated under reflux for 1 hour. After completion of the reaction, the reaction mixture was allowed to cool to room temperature. The crystals precipitated were collected by filtration to obtain 13.1 g of the desired compound. Melting point: 192° C.

Synthesis examples of compounds of the general formula I (the general formula I-4 )

Synthesis Example 12

Synthesis of N-(p-hydroxybenzoyl)-N'-n-octadecyloylhydrazine

In 300 ml of dimethylacetamide were dissolved 30.4 g of 4-hydroxybenzohydrazide and 21.0 g of triethylamine, followed by adding dropwise thereto 60.0 g of octadecyloyl chloride under ice-cooling. After completion of the dropwise addition, the resulting mixture was stirred at room temperature for 1 hour. Then, 500 ml of 1N HCl was added to the reaction mixture and the crystals precipitated were collected by filtration. The crystals thus obtained were washed with water, dried, washed with hot benzene, and then recrystallized from isopropanol to obtain 66.6 g of the desired compound in a pure form. Melting point: 162.5° C.

Synthesis Example 13

Synthesis of N-p-hydroxybenzoyl-N'-n-octadecanoylmethylenediamine

Into a 500-ml flask equipped with a stirrer and a condenser were charged 22.0 g of p-hydroxybenzamide, 25.0 g of N-methylolstearylamide, 1.5 ml of concentrated hydrochloric acid and 350 ml of tetrahydrofuran, and stirred with heating at 70° C. for 5 hours. The reaction mixture was cooled to room temperature and the crystals precipitated were collected by filtration. Recrystallization from isopropanol gave 33.1 g of white crystals of N-p-hydroxybenzoyl-N'-n-octadecanoylmethylenediamine. Melting point: 157.6° C.

Synthesis examples of compounds of the general formula II

Synthesis Example 14

Synthesis of the exemplified compound II-2

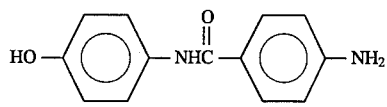

In 100 ml of dioxane was dissolved 5.3 g of stearoyl chloride, and a solution of 4.0 g of the above amine compound in 60 ml of N,N-dimethylformamide, and then 2.5 ml of triethylamine were added with stirring. The resulting mixture was stirred with heating at 90° C. for 3 hours. After completion of the reaction, the reaction mixture was allowed to stand at room temperature. The crystals precipitated were collected by filtration, and washed once with hot methanol and then twice with methanol to obtain 4.22 g of crystals of the exemplified compound II-2. Melting point: 262°–263° C.

Synthesis Example 15

Synthesis of the exemplified compound II-12

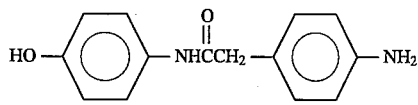

In 40 ml of N,N-dimethylformamide was dissolved 2.5 g of the above amine compound, and a solution of 3.1 g of stearoyl chloride in 40 ml of dioxane, and then 1.5 ml of triethylamine were added with stirring. The resulting mixture was stirred with heating at 90° C. for 4 hours. After completion of the reaction, the reaction mixture was allowed to stand at room temperature. The crystals precipitated were collected by filtration, and washed once with a small amount of dixane, twice with methanol and then once with benzene, and dried to obtain 3.0 g of crystals of the exemplified compound II-12. Melting point: 204°–205° C.

Synthesis examples of compounds of the general formula III

Synthesis Example 16

Synthesis of N-4-hydroxybenzono-N'-4-thiahexadecanohydrazide

Into a 200-ml flask equipped with a stirrer were charged 3.0 g of N-4-hydroxybenzonohydrazide, 2.0 g of triethylamine and 40 ml of dimethylacetamide, and stirred at room temperature. Into the resulting solution was slowly dropped 5.9 g of 4-thiahexadecanoyl chloride, upon which a precipitate was immediatly formed. The resulting mixture was stirred as it was for 30 minutes, and then poured into 400 ml of 1N hydrochloric acid. The crystals precipitated were collected by filtration and recrystallized from isopropanol to obtain 5.1 g of the desired compound. Melting point: 139.5° C.

Synthesis Example 17

Synthesis of N-4-hydroxybenzono-N'-12-thiadocosanohydrazide

Into a 200-ml flask equipped with a stirrer were charged 3.0 g of N-4-hydroxybenzonohydrazide, 2.0 g of triethylamine and 40 ml of dimethylacetamide, and stirred at room temperature. Into the resulting solution was slowly dropped 5.7 g of 11-bromoundecanoyl chloride, upon which a precipitate was immediatly formed. The resulting mixture was stirred as it was for 30 minutes, and then poured into 400 ml of 1N hydrochloric acid. The crystals precipitated were collected by filtration to obtain 7.5 g of N-4-hydroxybenzono-N'- 11-bromoundecanohydrazide. Subsequently, 4.0 g of the N-4-hydroxybenzono-N'-11-bromoundecanohydrazide, 1.7 g of decanethiol, 1.3 g of potassium hydroxide and 20 ml of ethanol were charged into a 100-ml flask equipped with a stirrer, and stirred with heating at 70° C. for 2 hours. The reaction mixture was cooled to room temperature and then poured into 200 ml of 1N hydrochloric acid. The crystals precipitated were collected by filtration and recrystallized from isopropanol to obtain 3.2 g of the desired compound. Melting point: 144° C.

Synthesis Example 18

Synthesis of N-3-(4-hydroxyphenyl)propano-N'-4-thiahexadecanohydrazide

Into a 100-ml flask equipped with a stirrer were charged 3.6 g of N-3-(4-hydroxyphenyl)propanohydrazide, 2.0 g of triethylamine and 40 ml of dimethylacetamide, and stirred at room temperature. Into the resulting solution was slowly dropped 5.9 g of 4-thiahexadecanoyl chloride, upon which a precipitate was immediatly formed. The resulting mixture was stirred as it was for 30 minutes, and then poured into 400 ml of 1N hydrochloric acid. The crystals precipitated were collected by filtration and recrystallized from isopropanol to obtain 6.0 g of the desired compound. Melting point: 169° C.

Synthesis Example 19

Synthesis of N-3-(4-hydroxyphenyl)propano-N'-12-thiadocosanohydrazide

Into a 200-ml flask equipped with a stirrer were charged 3.0 g of N-3-(4-hydroxyphenyl)propanohydrazide, 2.0 g of triethylamine and 40 ml of dimethylacetamide, and stirred at room temperature. Into the resulting solution was slowly dropped 5.7 g of 11-bromoundecanoyl chloride, upon which a precipitate was immediatly formed. The resulting mixture was stirred as it was for 30 minutes, and then poured into 400 ml of 1N hydrochloric acid. The crystals precipitated were collected by filtration to obtain 7.5 g of N-3-( 4-hydroxyphenyl)propano-N'-11-bromoundecanohydrazide. Subsequently, 4.0 g of the N-3-(4-hydroxyphenyl)propano-N'- 11-bromoundecanohydrazide, 1.7 g of decanethiol, 1.3 g of potassium hydroxide and 20 ml of ethanol were charged into a 100-ml flask equipped with a stirrer, and stirred with heating at 70° C. for 2 hours. The reaction mixture was cooled to room temperature and then poured into 200 ml of 1N hydrochloric acid. The crystals precipitated were collected by filtration and recrystallized from isopropanol to obtain 3.2 g of the desired compound. Melting point: 155° C.

Synthesis Example 20

Synthesis of N-11-(4-hydroxyphenylthia)undecano-N'-4-thiahexadecanohydrazide Into a 200-ml flask equipped with a stirrer were charged 3.2 g of N-11-(4-hydroxyphenylthia)-undecanohydrazide, 1.1 g of triethylamine and 40 ml of dimethylacetamide, and stirred at room temperature. Into the resulting solution was slowly dropped 5.9 g of 4-thiahexadecanoyl chloride, upon which a precipitate was immediatly formed. The resulting mixture was stirred as it was for 30 minutes and then at 100° C. for 30 minutes, and poured into 400 ml of 1N hydrochloric acid. The crystals precipitated were collected by filtration and recrystallized from isopropanol to obtain 4.0 g of the desired compound. Melting point: 157° C.

The present invention is illustrated in further detail with the following examples.

EXAMPLE 1

(A) Preparation of a reversible heat-sensitive coating fluid

Using a ball mill, 40 parts of 3-di-n-butylamino- 6-methyl-7-anilinofluoran as dye precursor was ground for 24 hours together with 90 parts of a 2.5% aqueous polyvinyl alcohol solution to obtain a dye precursor dispersion. Then, 100 parts of N-[2-(p-hydroxyphenyl)aceto]-N'-n-octadecanohydrazide was ground with a ball mill for 24 hours together with 400 parts of a 2.5% aqueous polyvinyl alcohol solution to obtain a dispersion. The above two dispersions were mixed and 200 parts of a 10% aqueous polyvinyl alcohol solution and 400 parts of water were thoroughly mixed therewith to prepare a reversible heat-sensitive coating fluid.

(B) Production of a reversible heat-sensitive recording material

The reversible heat-sensitive coating fluid prepared in (A) was applied on a polyethylene terephthalate (PET) sheet to adjust the amount of coating to 4 g/m2 in terms of solids, dried and then supercalendered to obtain a reversible heat-sensitive recording material.

EXAMPLES 2 to 11 and Comparative Examples 1 to 3

Reversible heat-sensitive recording materials were obtained in the same manner as in Example 1 except for using each of the following compounds in place of N-[2-(p-hydroxyphenyl)aceto]-N'-n-octadecanohydrazide:

(Example 2) N-[3-(p-hydroxyphenyl)propiono]-N'-n-docosanohydrazide, (Example 3) N-[5-(p-hydroxyphenyl)valeryl]-N'-n-docosanohydrazide, (Example 4) 1-(p-hydroxyphenyl)acetamido-1-n-octadecanoylaminomethane, (Example 5) N-[2-(p-hydroxyphenyl)ethyl]-N'-n-octadecyloxamide, (Example 6) N-[3-(p-hydroxyphenyl)propionyl]-N'-n-octadecylurea, (Example 7) 4-[2-(p-hydroxyphenyl)ethyl-1-n-octadecanoylsemicarbazide, (Example 8) 1-[3-(p-hydroxyphenyl)propionyl]-4-n-octadecylsemicarbazide, (Example 9) [2-(p-hydroxyphenyl)ethyl]N-n-octadecylcarbamate, (Example 10) 1-[2-(p-hydroxyphenyl)acetamido]-1-n-tetradecanoylaminomethane, (Example 11) 1-[3-(p-hydroxyphenyl)propanamido]-1-(N'-n-octadecylureido)methane, (Comparative Example 1) salt of gallic acid and stearylamine, (Comparative Example 2) 2,2-bis(p-hydroxyphenyl)propane, and (Comparative Example 3) p-(n-octadecylthio)phenol.

Test 1 (Coloring density =thermal response)

Each of the heat-sensitive recording materials obtained in Examples 1 to 11 and Comparative Examples 1 to 3 was subjected to printing under conditions of an applied pulse of 1.1 msec and an applied voltage of 26 V by the use of a heat-sensitive facsimile printing tester TH-PMD (mfd. by Ohkura Denki K.K.) equipped with a print head KJT-256-8MGF1 (mfd. by Kyocera Co. Ltd.). The color density of the resulting developed color image was measured by means of a densitometer Macbeth RD918. The results obtained are shown in Table 1.

Test 2 (Change of coloring density with time =image stability)

Each of the heat-sensitive recording materials obtained in Examples 1 to 11 and Comparative Examples 1 to 3 was subjected to printing under conditions of an applied pulse of 1.1 msec and an applied voltage of 26 V by the use of a heat-sensitive facsimile printing tester TH-PMD (mfd. by Ohkura Denki K.K.) equipped with a print head KJT-256-8MGF1 (mfd. by Kyocera Co. Ltd.), and then stored in an atmosphere of 60° C. and 30% R.H. for 14 hours. Thereafter, the color density of the colored portion was measured in the same manner as in Test 1 and the image survival rate was calculated by the following equation. The results obtained are shown in Table 1.

$$A=(C/B)\times 100$$

wherein

A: image survival rate (%),

B: coloring density before the test,

C: coloring density after the test.

Test 3 (Erasability of image)

Each of the heat-sensitive recording materials obtained in Examples 1 to 11 and Comparative Examples 1 to 3 was subjected to printing under conditions of an applied pulse of 1.1 msec and an applied voltage of 26 V by the use of a heat-sensitive facsimile printing tester TH-PMD (mfd. by Ohkura Denki K.K.) equipped with a print head KJT-256-8MGF1 (mfd. by Kyocera Co. Ltd.). The resulting developed color image portion was heated at 120° C. for 1 second with a heating stamp, after which its color density was measured in the same manner as in Test 1. The results obtained are shown in Table 1.

TABLE 1

|  | Test 1 Color density of colored portion | Test 2 Image survival rate | Test 3 Color density of erased image portion | Contrast |
| --- | --- | --- | --- | --- |
| Example 1 | 1.22 | 92% | 0.07 | ○ |
| Example 2 | 1.31 | 99% | 0.08 | ○ |
| Example 3 | 1.42 | 99% | 0.06 | ○ |
| Example 4 | 1.20 | 90% | 0.08 | ○ |
| Example 5 | 1.14 | 91% | 0.06 | ○ |
| Example 6 | 1.14 | 80% | 0.16 | ○ |
| Example 7 | 1.28 | 90% | 0.06 | ○ |
| Example 8 | 1.21 | 91% | 0.07 | ○ |
| Example 9 | 1.17 | 80% | 0.16 | ○ |
| Example 10 | 1.24 | 85% | 0.16 | ○ |
| Example 11 | 1.27 | 92% | 0.06 | ○ |
| Comparative Example 1 | 0.47 | 41% | 0.23 | Δ |
| Comparative Example 2 | 1.37 | 96% | 1.28 | x |
| Comparative Example 3 | 0.68 | 31% | 0.26 | Δ |

In Table 1, ○ indicates that the color density of an erased image portion is less than 30% of that of a colored portion, namely, the contrast between the colored portion and the erased image portion is satisfactory; Δ indicates that the color density of an erased image portion is not more than 80% and not less than 30% of that of a colored portion, namely, the contrast is not sufficient; and x indicates that the color density of an erased image portion is more than 80% of that of a colored portion, namely, no reversibility is observed.

EXAMPLES 12 to 17 and Comparative Examples 4 to 6

Reversible heat-sensitive recording materials were obtained in the same manner as in Example 1 except for using each of the following compounds in place of N-[2-(p-hydroxyphenyl)aceto]-N'-n-octadecanohydrazide:

(Example 12) N-(p-hydroxyphenyl)-N'-n-octadecylmalonamide, (Example 13) N-(p-hydroxyphenyl)-N'-oleylmalonamide, (Example 14) N-(p-hydroxyphenyl)-N'-(n-octadecyloxyphenyl)malonamide, (Example 15) N-(p-hydroxyphenyl)-N'-n-octadecyloxamide, (Example 16) N-(p-hydroxyphenyl)-N'-oleyloxamide, (Example 17) N-(P-hydroxyphenyl)-N'-(n-octadecyloxyphenyl)oxamide, (Comparative Example 4) salt of gallic acid and stearylamine, (Comparative Example 5) 2,2-bis(p-hydroxyphenyl)propane, and (Comparative Example 6) p-(n-octadecylthio)phenol.

Test

The heat-sensitive recording materials obtained in Examples 12 to 17 and Comparative Examples 4 to 6 were tested in the same manner as in Tests 1 to 3 carried out in Examples 1 to 11 and Comparative Examples 1 to 3, except for changing the storing temperature of 60° C. employed in Test 2 to 50° C. The results obtained are shown in Table 2. The symbols ○, Δ and x used for expressing the contrast in Table 2 are as defined in Table 1.

TABLE 2

|  | Test 1 Color density of colored portion | Test 2 Image survival rate | Test 3 Color density of erased image portion | Contrast |
| --- | --- | --- | --- | --- |
| Example 12 | 1.18 | 92% | 0.07 | ○ |
| Example 13 | 1.14 | 84% | 0.08 | ○ |
| Example 14 | 1.21 | 80% | 0.07 | ○ |
| Example 15 | 1.07 | 95% | 0.06 | ○ |
| Example 16 | 1.10 | 81% | 0.06 | ○ |
| Example 17 | 1.17 | 80% | 0.06 | ○ |
| Comparative Example 4 | 0.47 | 41% | 0.23 | Δ |
| Comparative Example 5 | 1.37 | 96% | 1.28 | x |
| Comparative Example 6 | 0.68 | 31% | 0.26 | Δ |

EXAMPLES 18 to 23 and Comparative Examples 7 to 10

Reversible heat-sensitive recording materials were obtained in the same manner as in Example 1 except for using each of the following compounds in place of N-[2-(p-hydroxyphenyl)aceto]-N'-n-octadecanohydrazide:

(Example 18) N-(4-hydroxybenzoyl)-N'-n-tetradecanoylhydrazine, (Example 19) N-(4-hydroxybenzoyl)-N'-n-octadecanoylhydrazine, (Example 20) N-(2,4-dihydroxybenzoyl)-N'-n-octadecanoylhydrazine, (Example 21) N-(4-hydroxybenzoyl)-N'-n-octadecylaminocarbonylhydrazine, (Example 22) N-(4-hydroxybenzoyl)-N'-n-octadecanoylmethylenediamine, (Example 23) N-(4-hydroxybenzoyl)-N'-n-octadecylaminocarbonylmethylenediamine, (Comparative Example 7) salt of gallic acid and stearylamine, (Comparative Example 8) 2,2-bis(p-hydroxyphenyl)propane, (Comparative Example 9) benzyl 4-hydroxybenzoate, and (Comparative Example 10) octadecylphosphonic acid.

Test

The heat-sensitive recording materials obtained in Examples 18 to 23 and Comparative Examples 7 to 10 were subjected to Tests 1 to 3 carried out in Examples 1 to 11 and Comparative Examples 1 to 3, in the same manner as in these examples and comparative examples except for changing the storing temperature of 60° C. employed in Test 2 to 35° C. The results obtained are shown in Table 3. The symbols ○, Δ and x used for expressing the contrast in Table 3 are as defined in Table 1.

TABLE 3

|  | Test 1 Color density of colored portion | Test 2 Image survival rate | Test 3 Color density of erased image portion | Contrast |
| --- | --- | --- | --- | --- |
| Example 18 | 1.40 | 98% | 0.15 | ○ |
| Example 19 | 1.40 | 99% | 0.10 | ○ |
| Example 20 | 1.38 | 98% | 0.15 | ○ |
| Example 21 | 1.35 | 96% | 0.10 | ○ |
| Example 22 | 1.40 | 98% | 0.12 | ○ |
| Example 23 | 1.38 | 95% | 0.10 | ○ |
| Comparative Example 7 | 0.47 | 53% | 0.23 | Δ |
| Comparative Example 8 | 1.37 | 96% | 1.28 | x |
| Comparative Example 9 | 1.33 | 68% | 1.18 | x |
| Comparative Example 10 | 1.33 | 78% | 0.68 | Δ |

EXAMPLES 24 to 34 and Comparative Examples 11 to 13

Reversible heat-sensitive recording materials were obtained in the same manner as in Example 1 except for using each of the following compounds in place of N-[2-(p-hydroxyphenyl)aceto]-N'-n-octadecanohydrazide:

(Example 24) N-[2-(p-hydroxyphenylthio)ethyl]-N'-octadecylurea, (Example 25) N-[10-N-[p-(p-hydroxyphenylthio)phenyl]-N'-n-tetradecylurea, (Example 26) N-[3-(p-hydroxyphenylthio)decyl]-N'-n-decylurea, (Example 27) N-[11-(p-hydroxyphenylthio)propiono]-N'-octadecanohydrazide, (Example 28) N-[10-(p-hydroxyphenylthio)undecano]-N'-n-n-decanohydrazide, (Example 29) N-[p-(p-hydroxyphenylthio)benzo]-N'-n-tetradecanohydrazide, N-[3-(p-hydroxyphenylthio)propyl]-N'-n-

(Example 30) N-[p-(p-hydroxyphenylthio)phenyl]-N'-n-octadecyloxamide, (Example 31) 1-[3-(p-hydroxyphenylthio)propionyl]-4-octadecyloxamide, (Example 32) 1-[2-(p-hydroxyphenylthio)acetamido]-1-n-tetradecylsemicarbazide, (Example 33) 1-[2-(p-hydroxyphenylthio)acetamido]-1-n-tetradecanoylaminomethane, (Example 34) 1-[3-(p-hydroxyphenylthio)propanamide]-1-[ 2-(p-hydroxyphenylthio)acetamido]-1-1-(N'-n-octadecylureido)methane, (Comparative Example 11) salt of gallic acid and stearylamine, (Comparative Example 12) 2,2-bis(p-hydroxyphenyl)propane, and (Comparative Example 13) p-(n-octadecylthio)phenol.

Test

The heat-sensitive recording materials obtained in Examples 24 to 34 and Comparative Examples 11 to 13 were subjected to Tests 1 to 3 in the same manner as in Examples 12 to 17 and Comparative Examples 4 to 6 except for changing the storing temperature of 60° C. employed in Test 2 to 50° C. The results obtained are shown in Table 4. The symbols ○, Δ and x used for expressing the contrast in Table 4 are as defined in Table 1.

TABLE 4

|  | Test 1 Color density of colored portion | Test 2 Image survival rate | Test 3 Color density of erased image portion | Contrast |
| --- | --- | --- | --- | --- |
| Example 24 | 1.29 | 85% | 0.16 | ○ |
| Example 25 | 1.41 | 88% | 0.19 | ○ |
| Example 26 | 1.42 | 96% | 0.21 | ○ |
| Example 27 | 1.30 | 95% | 0.14 | ○ |
| Example 28 | 1.40 | 99% | 0.10 | ○ |
| Example 29 | 1.33 | 92% | 0.11 | ○ |
| Example 30 | 1.28 | 90% | 0.09 | ○ |
| Example 31 | 1.41 | 91% | 0.07 | ○ |
| Example 32 | 1.27 | 90% | 0.09 | ○ |
| Example 33 | 1.29 | 96% | 0.12 | ○ |
| Example 34 | 1.27 | 92% | 0.14 | ○ |
| Comparative Example 11 | 0.47 | 53% | 0.23 | Δ |
| Comparative Example 12 | 1.37 | 96% | 1.28 | x |
| Comparative Example 13 | 0.68 | 41% | 0.26 | Δ |

EXAMPLES 35 to 40 and Comparative Examples 14 to 17

Reversible heat-sensitive recording materials were obtained in the same manner as in Example 1 except for using each of the following compounds in place of N-[2-(P-hydroxyphenyl)aceto]-N,-n-octadecanohydrazide:

(Example 35) the exemplified compound II-12, (Example 36) the exemplified compound II-4, (Example 37) the exemplified compound II-15, (Example 38) the exemplified compound II-18, (Example 39) the exemplified compound II-19, (Example 40) the exemplified compound II-31, (Comparative Example 14) salt of gallic acid and stearylamine, (Comparative Example 15) 2,2-bis(p-hydroxyphenyl)propane, (Comparative Example 16) benzyl 4-hydroxybenzoate, and (Comparative Example 17) p-octadecylthiophenol.

Test

The heat-sensitive recording materials obtained in Examples 35 to 40 and Comparative Examples to 17 were subjected to Tests 1 to 3 in the same manner as in Examples 12 to 17 and Comparative Examples 4 to 6 except for changing the storing temperature of 60 ° C. employed in Test 2 to 50° C. The results obtained are shown in Table 5. The symbols ○, Δ and x used for expressing the contrast in Table 5 are as defined in Table 1.

TABLE 5

|  | Test 1 Color density of colored portion | Test 2 Image survival rate | Test 3 Color density of erased image portion | Contrast |
| --- | --- | --- | --- | --- |
| Example 35 | 1.38 | 97% | 0.13 | ○ |
| Example 36 | 1.39 | 96% | 0.11 | ○ |
| Example 37 | 1.43 | 98% | 0.10 | ○ |

TABLE 5-continued

|  | Test 1 Color density of colored portion | Test 2 Image survival rate | Test 3 Color density of erased image portion | Contrast |
|---|---|---|---|---|
| Example 38 | 1.42 | 98% | 0.11 | ○ |
| Example 39 | 1.40 | 97% | 0.12 | ○ |
| Example 40 | 1.40 | 96% | 0.11 | ○ |
| Comparative Example 14 | 0.46 | 52% | 0.22 | Δ |
| Comparative Example 15 | 1.37 | 95% | 1.30 | x |
| Comparative Example 16 | 1.35 | 65% | 1.19 | x |
| Comparative Example 17 | 0.65 | 40% | 0.25 | Δ |

EXAMPLES 41 to 45 and Comparative Examples 18 to 20

Reversible heat-sensitive recording materials were obtained in the same manner as in Example 1 except for using each of the following compounds in place of N-[2-(P-hydroxyphenyl)aceto]-N'-n-octadecanohydrazide:

(Example 41) N-4-hydroxybenzono-N'-4-thiahexadecanohydrazide, (Example 42) N-4-hydroxybenzono-N'-12-thiadocosanohydrazide, (Example 43) N-3-(4-hydroxyphenyl)propano-N,-4-thiahexadecanohydrazide, (Example 44) N-3-(4-hydroxyphenyl)propano-N'-12-thiadocosanohydrazide, (Example 45) N-11-(4-hydroxyphenylthia)undecano-N'-4-thiahexadecanohydrazide, (Comparative Example 18) salt of gallic acid and stearylamine, (Comparative Example 19) 2,2-bis(p-hydroxyphenyl)propane, and (Comparative Example 20) p-(n-octadecylthio)phenol.

Test

The heat-sensitive recording materials obtained in Examples 41 to 45 and Comparative Examples 18 to 20 were subjected to Tests 1 to 3 in the same manner as in Examples 12 to 17 and Comparative Examples 4 to 6 except for changing the storing temperature of 60° C. employed in Test 2 to 50° C. The results obtained are shown in Table 6. The symbols ○, Δ and x used for expressing the contrast in Table 6 are as defined in Table 1.

TABLE 6

|  | Test 1 Color density of colored portion | Test 2 Image survival rate | Test 3 Color density of erased image portion | Contrast |
|---|---|---|---|---|
| Example 41 | 1.29 | 85% | 0.16 | ○ |
| Example 42 | 1.40 | 94% | 0.19 | ○ |
| Example 43 | 1.35 | 89% | 0.21 | ○ |
| Example 44 | 1.40 | 96% | 0.14 | ○ |
| Example 45 | 1.36 | 88% | 0.10 | ○ |
| Comparative Example 18 | 0.47 | 53% | 0.23 | Δ |
| Comparative Example 19 | 1.37 | 96% | 1.28 | x |
| Comparative Example 20 | 0.68 | 41% | 0.26 | Δ |

What is claimed is:

1. Reversible heat-sensitive recording material comprising a substrate and a recording layer formed thereon, said recording layer comprising a colorless or light-colored, electron-donating dye precursor and an electron-accepting compound represented by the following general formula which causes a reversible color tone change of the dye precursor on heating:

$$(HO)_n\text{-Ar-}(S)_p\text{-}(R^1)_q\text{-}X^1\text{-}R^2 \quad \text{I}$$

wherein n is an integer of 1 to 3, each of p and q is zero or 1, $R^1$ is a divalent hydrocarbon group having 1 to 18 carbon atoms, $R^2$ is a hydrocarbon group having 1 to 24 carbon atoms, and $X^1$ is a divalent group having at least one amide bond, $X^1$ not including a mere amide and a urea bond in the case of p being zero, and q being 1 in the case of p being 1.

2. Reversible heat-sensitive recording material according to claim 1, wherein the divalent group of $X^1$ in the formula I is selected from the group consisting of urethane, diacylamine, diacylhydrazine, oxalic diamide, acylurea, semicarbazide, acylsemicarbazide, diacylaminomethane, 1-acylamino-1-ureidomethane, malonamide, amide, urea, and groups represented by the general formula IV:

$$-\underset{\underset{O}{\|}}{C}-NH-(CH_2)_z-NH-\underset{\underset{O}{\|}}{C}-X^4$$

wherein z is zero or 1, and $X^4$ is an oxygen atom or a —NHNH— group.

3. Reversible heat-sensitive recording material according to claim 1, wherein the electron accepting compound represented by formula I has one of the following general formulas I-1 to I-4:

$$(HO)_n\text{-Ar-}R^1\text{-}X^5\text{-}R^2 \quad \text{I-1}$$

$$(HO)_n\text{-Ar-}S\text{-}R^1\text{-}X^3\text{-}R^2 \quad \text{I-2}$$

$$(HO)_n\text{-Ar-}NH-\underset{\underset{O}{\|}}{C}-(CH_2)_z-\underset{\underset{O}{\|}}{C}-NH-R^2 \quad \text{I-3}$$

$$(HO)_n\text{-Ar-}\underset{\underset{O}{\|}}{C}-NH-(CH_2)_z-NH-\underset{\underset{O}{\|}}{C}-X^6-R^2 \quad \text{I-4}$$

wherein the above general formulas I-1 to I-4, n, $R^1$ and $R^2$ are defined in the general formula I, $X^3$ os a divalent group having at least one amide bond, $X^5$ has the same meaning at that given to $X^1$ in the general formula I in the case of p being zero, z is zero or 1, and $X^6$ is a methylene group, an oxygen atom, a —NH— group or a —NHNH— group.

4. Reversible heat-sensitive recording material comprising a substrate and a recording layer formed thereon, said recording layer comprising a colorless or light-colored, electron-donating dye precursor and an electron-accepting compound represented by the following general formula II which causes a reversible color tone change of the dye precursor on heating:

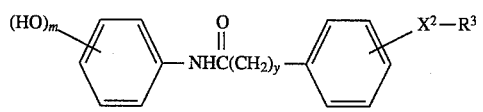

wherein m is 1 or 2, y is an integer of 0 to 2, $X^2$ is a divalent group having at least one amide bond, and $R^3$ is an aliphatic hydrocarbon group.

5. Reversible heat-sensitive recording material according to claim 4, wherein the divalent group of $X^2$ in the formula II is selected from the group consisting of —NHCO— group, —CONH— group, —NHCONH— group, —NHCOCONH— group, —CONHNHCO— group, —CONHNHCONH— group, —CONHNHCOO— group, —OCONH— group, or —NHCOO— group.

6. Reversible heat-sensitive recording material comprising a substrate and a recording layer formed thereon, said recording layer comprising a colorless Or light-colored, electron-donating dye precursor and an electron-accepting compound represented by the following general formula III which causes a reversible color tone change of the dye precursor on heating:

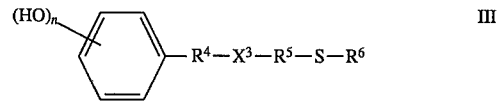

wherein n is an integer of 1 to 3, $R^4$ is a single bond or a divalent hydrocarbon group having 1 to 12 carbon atoms, $R^5$ is a divalent hydrocarbon group having 1 to 12 carbon atoms, $R^6$ is a hydrocarbon group having 1 to 24 carbon atoms, and $X^3$ is a divalent group having at least one amide bond.

7. Reversible heat-sensitive recording material according to claim 6, wherein the divalent group of $X^3$ in the formula III is selected from the group consisting of amide, urea, diacylamine, diacylhydrazine, oxalic diamide, acylurea, semicarbazide, acylsemicarbazide, diacylaminomethane, 1-acylamino-1-ureidomethane, and malonamide.

\* \* \* \* \*